United States Patent [19]

Oppawsky et al.

[11] Patent Number: 5,040,964
[45] Date of Patent: Aug. 20, 1991

[54] APPARATUS FOR POLYMERIZATION OF PLASTIC DENTAL MATERIAL

[75] Inventors: Steffen Oppawsky, Bad Homburg, Fed. Rep. of Germany; Peter Fischer, Zürich, Switzerland

[73] Assignee: Heraeus Kulzer GmbH, Wehrheim, Fed. Rep. of Germany

[21] Appl. No.: 503,227

[22] Filed: Apr. 2, 1990

[30] Foreign Application Priority Data

Mar. 31, 1989 [DE] Fed. Rep. of Germany ....... 3910438

[51] Int. Cl.$^5$ ............................................ B29C 35/08
[52] U.S. Cl. ................................... 425/135; 264/16; 264/22; 264/40.1; 425/174.4; 425/162
[58] Field of Search .......................... 264/40.1, 16, 22; 425/135, 174, 174.4, 162; 356/72, 215, 218; 250/492.1

[56] References Cited

U.S. PATENT DOCUMENTS

| | | | |
|---|---|---|---|
| 3,851,970 | 12/1974 | Adler et al. | 356/218 |
| 4,569,717 | 2/1986 | Ohgami et al. | 356/72 |
| 4,666,301 | 5/1987 | Gruenke | 356/218 |
| 4,682,595 | 7/1987 | Hoererz et al. | 356/215 |
| 4,890,997 | 1/1990 | Bains et al. | 425/174 |

FOREIGN PATENT DOCUMENTS

G8320883 11/1983 Fed. Rep. of Germany .
3405049 8/1985 Fed. Rep. of Germany .

Primary Examiner—Jay H. Woo
Assistant Examiner—Robert B. Davis
Attorney, Agent, or Firm—Frishauf, Holtz, Goodman & Woodward

[57] ABSTRACT

The present invention is an improvement upon a known apparatus for polymerization of a body from dental plastic material by irradiation of the body with radiation of a selected wave length in the range between about 350 nm and about 550 nm. To achieve a desired degree of polymerziation of the dental plastic, a specific amount of radiation must be applied to the body. In order to achieve reproducible irradiation results in spite of fluctuations in supply voltage, alterations in lamp characteristics, burn out of one or more lamps, shifting of spectral outputs, replacement of defective or superannuated lamps, soiling of lamps and reflector surfaces and/or changes of operating temperatures in the irradiation area, a supplemental detection system in provided. Upon beginning of irradiation, a photocell measures a percentage component of the radiation within the selected wave length range from each irradiation source, generates an electrical signal therefrom and the electrical signal is integrated and compared to a predetermined value corresponding to the desired degree of polymerization. When the predetermined value is reached, the irradiation is interrupted.

14 Claims, 3 Drawing Sheets

APPARATUS FOR POLYMERIZATION OF PLASTIC DENTAL MATERIAL

CROSS REFERENCE TO RELATED PATENT DOCUMENTS

German Patent Disclosure Document DE-OS 34 05 049, HEROLD & KELLER/ESPE, published Aug. 14, 1985; German Utility Model G 83 20 883.6, KULZER & CO. GmbH, published Nov. 17, 1983.

FIELD OF THE INVENTION

The present invention relates generally to polymerization of dental plastic by irradiation and, more particularly, to a method and apparatus for obtaining the optimum degree of polymerization by automatically taking measurements during the irradiation process and turning off the radiation source when a predetermined measured value is reached. The method is particularly adapted to irradiation of dental plastic monomers with light in the selected wave length range of 350 nanometers to 550 nanometers, from at least one light source, the desired degree of polymerization of the dental plastic being achieved by application of a predetermined amount of irradiation to the plastic body. Further, the invention includes an apparatus for carrying out the method, the apparatus including a sample holder for the body to be polymerized, one or more light sources associated with the sample holder, which sources emit light in the wave length band between about 350 nm and 550 nm, and with an electrical or electronic control unit.

Such a method, and a corresponding apparatus, are described in German Patent Disclosure Document DE-OS 34 05 049, HEROLD & KELLER. This published unexamined application discloses a device for irradiation of dentures and dental raw materials. Adjacent to the sample holder, a light beam detector 16, 17 is provided which actuates a timing element 27, whenever an object is brought into the light path of the detector. Timing element 27 maintains the lamp or lamps in the ON state for a predetermined minimum time period. If the object being hardened or cured is removed from the sample holder during this minimum time period, a signal transducer is activated, which is switched off again upon re-entrance of the object into the treatment area. Upon shutting off of the signal transducer, the lamps are turned on again, so that the irradiation of the object is continued. These measures are designed to avoid the danger of insufficient hardening of the dentures or dental materials to be irradiated.

German utility model DE-GM 83 20 883, registered Nov. 17, 1983 to KULZER and Co. G.m.b.H., discloses a polymerization device for the dental industry in which the material to be polymerized is placed on a sample holder which is surrounded by multiple irradiation lamps. This apparatus also permits setting of a predetermined necessary irradiation time, upon expiration of which the device shuts off.

Experience has shown that it is very difficult to obtain a reproducible amount of irradiation and thus equal hardening or curing of objects, because of fluctuations in the supply voltage, changes in the lamps, burning out of one or multiple lamp(s), shifting of the emitted light wave length, replacement of defective or superannuated lamps, soiling of lamp and reflector surfaces, and/or changes of the operating temperatures in the irradiation zone.

THE INVENTION

It is an object of the present invention to provide a method and an apparatus for carrying out the method which will make possible a reproducible amount of irradiation, by compensating for the aforementioned circumstances which lead to changes in the irradiation conditions.

Briefly, upon starting of the irradiation of the body, a photocell measures and a device integrates the percentage component of the irradiation of the selected wave length range coming from each radiation source and generates an electrical signal. During irradiation, the electrical signal is integrated. Upon reaching a predetermined value which corresponds to the desired degree of polymerization, the irradiation is interrupted. In the apparatus according to the invention, the photocell is so located, adjacent to the light source(s), that a percentage component of the selective radiation of each radiation source falls on it, that the photocell is positioned in relation to the body in such a way that no radiation component from the area of the body falls on the photocell, and that the control unit has an input connected with the photocell and an output connected to and controlling the radiation sources.

According to the method of the invention, the amount of radiation of each radiation source, or at least a percentage component thereof, is continuously measured by a photocell and, from this radiation amount, a corresponding signal is integrated or added up. This means, that, for example, upon diminuition of the light output of a lamp, the signal per unit time deriving from the light output also diminishes, and that the overall irradiation time must be lengthened to compensate. The irradiation time is thus determined in dependence upon the radiation amount generated by the radiating lamps and that the irradiation process is only interrupted or ended, once a predetermined amount of radiation has been applied to the body being treated. With this method, a reproducible irradiation is possible from exposure to exposure, for example of identical bodies to be irradiated or cured. In carrying out this method, it is necessary to assure that only radiation coming from the radiation sources is measured in a percentage component and that light reflected from the body or from other objects in the area of the body are not factored into this measurement of the amount of radiation. Otherwise, a false reading of the amount of radiation coming from the radiation sources will result.

According to a further feature of the method, the integrated value of the radiation corresponding to the desired degree of polymerization is used to derive an electrical signal, which serves as the signal or trigger for the interruption of the power supply of the radiation source or radiation sources. Since the polymerization of the dental plastic is only effectuated by irradiation of a selective wave length range which falls between about 350 nm and 550 nm, the irradiation reaching the photocell is filtered so that the photocell measures only radiation within this wavelength range.

In the apparatus for carrying out the method, the photocell is so positioned that it can detect only radiation components of the individual radiation sources or of each radiation source and the reflectors. Radiation components which come as reflections from the area of the body being irradiated thus may not reach the photocell. Depending upon the arrangement of the radiation sources, one or more screens are arranged adjacent to the photocell in order to screen the photocell against reflection from the body.

There is the possibility in a radiation system having multiple radiation sources, to associate, with each radiation source, a photocell which measures or detects the radiation amount of this respective individual radiation source. In the simplest embodiment, only a single photocell is provided which, to the extent possible, is arranged centrally with identical spacing from each radiation source. In order to direct a percentage radiation component of each radiation source onto the photocell, a reflector is located between the photocell and the screen with its reflective surface facing the photocell.

Further, in order to define the wavelength range required for polymerization, one or more filters which are transmissive in this wavelength range are located between the photocell and the screen. In order to simplify arrangement of the photocell, the screen and/or the reflector with respect to each other, the photocell is located on a first end of a light conduit, and the screen and/or the reflector are located on the opposite or remote end of this light conduit. Such a light conduit can, for example, be a bundle of optical fibers; preferably, the light conduit is arranged in the form of a solid cylinder or a hollow cylinder. Both the solid cylinder and the hollow cylinder can comprise a glass material, preferably quartz glass. There is of course also a possibility to provide a hollow cylinder of non-transparent material, having windows or slits arranged circumferentially, associated with the individual radiation sources, in order to let the radiation into the cylinder. The inner surfaces of the cylinder must be mirrored, so that the radiation entering through the windows or slits will be reflected to the photocell. Preferably, an arrangement of the radiation apparatus is chosen in which the photocell is located centrally over the sample holder and the radiation sources are positioned at identical spaces to the axis defined between the center of the sample holder and of the photocell.

Preferably the reflective surfaces of the reflective form a cone, with the point of the cone being directed to the center of a photocell. In conjunction with a light conduit in the form of hard cylinder, such a reflective surface is defined by a conical tapping at the end face of the cylinder, which face is coated with a reflective material. In conjunction with a hollow cylinder as light conduit, a conical reflector is inserted into the end of the hollow cylinder. The base or support surface of such a conical reflector can simultaneously be enlarged so that is serves as the screen for shading of the photocell with respect to the body being irradiated.

The control unit connected downstream of the photocell, which forms the connecting element between the photocell and the radiation sources and which detects and evaluates the radiation amount needed for hardening, includes an amplifier, whose output is connected to the input of a voltage to frequency converter. The output of the converter is connected to a digital actual value counter. The counter is connected to a digital preset value memory and has an output connected to the radiation sources. According to a preferred embodiment, the actual value counter is connected via a start-/stop unit with the radiation source or sources.

The irradiation is measured by means of the photocells and filters in the spectral range which is necessary for the hardening. In the photocell, a signal proportional to the intensity of light is generated. This voltage signal is amplified in the downstream amplifier. In the subsequent voltage to frequency converter, this voltage is transformed into an intensity-dependent frequency. This frequency can be arbitrarily divided into another value for subsequent processing, e.g. for comparison with the predetermined "preset" value in a digital command value memory. Upon reaching of this preset value or threshold, the power supply of the irradiation sources is interrupted. If the intensity of light detected by the photocell deviates positively or negatively, for example due to alterations in the radiating lamps, the pulses per time deviate correspondingly, so that the radiation time for achievement of the predetermined number of pulses is adjusted accordingly. For example, if it normally takes 400 seconds to complete polymerization of a body to be hardened, a reduction of the effective intensity of 10% will result in a lengthening of the irradiation time by 10%. The amount of radiation applied to the body during each irradiation process thus is maintained always at the same value.

DETAIL DESCRIPTION OF THE DRAWINGS

Figure 1:
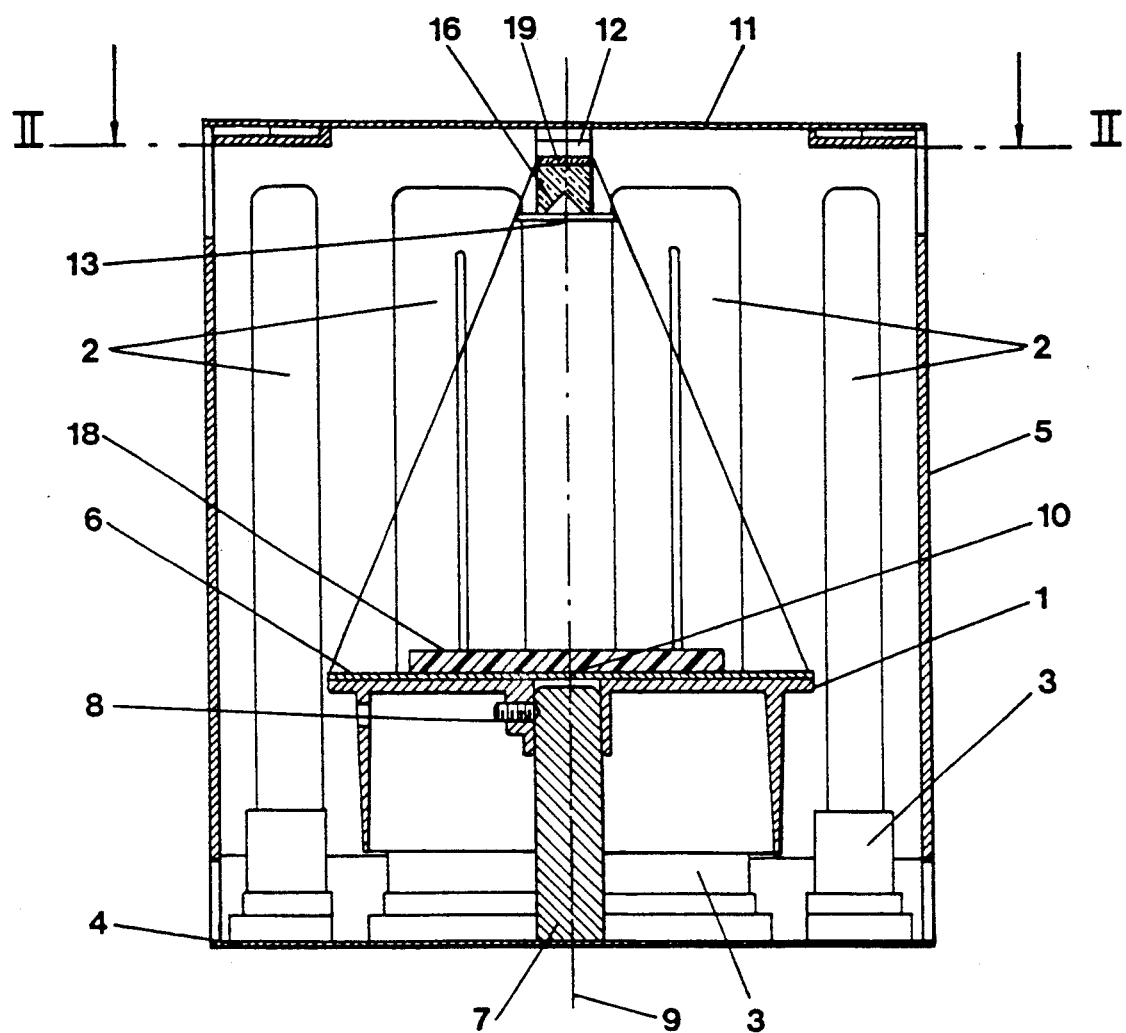
FIG. 1 is a vertical section through the axis of an irradiation device according to the present invention.
Figure 2:
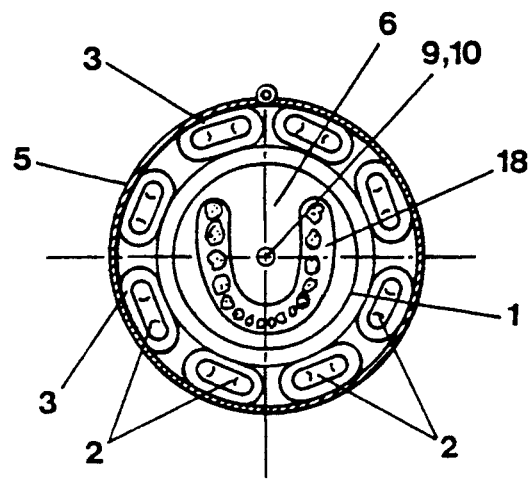
FIG. 2 is a cross section along line II—II of FIG. 1.

As shown in FIGS. 1 and 2, the irradiation device has a sample holder 1 which is surrounded by multiple individually based radiation sources or irradiation lamps 2. The individual sockets 3 of the respective irradiation lamps 2 are fastened on a base plate 4 of a housing 5. The sample holder 1 is arranged in housing 5 with its receiving or support surface 6 above the sockets 3. Housing 5 consists of two half-shells which can be brought together. The sample holder 1 can be swapped in and out and is placed on a pin 7, onto which it can be fastened by means of a set screw 8. The sample holder can also be in the form of a rotatable plate.

Above sample holder 1, along the extension of axis 9 of pin 7, which axis passes through the middle 10 of the disk shaped sample holder 1, is a ceiling 11 of the housing, to which is attached to a photocell 12. Preferably, there are 8 irradiation lamps 2 at identical spacings from axis 9 and thus at identical spacings from photocell 12. The photocell detects a percentage component of the selective radiation of each radiation source in the wave length range from about 350 nanometers to about 550 nanometers (nm). To assure that photocell 12 detects only the radiation of the irradiation lamps 2, shown schematically in FIG. 3 on each side of sample holder 1 and designated in FIGS. 1 and 2 with reference numerals 2, the photocell is protected by a screen 13. In the embodiment illustrated, screen 13 is a flat element parallel to sample holder 1.

Figure 3:
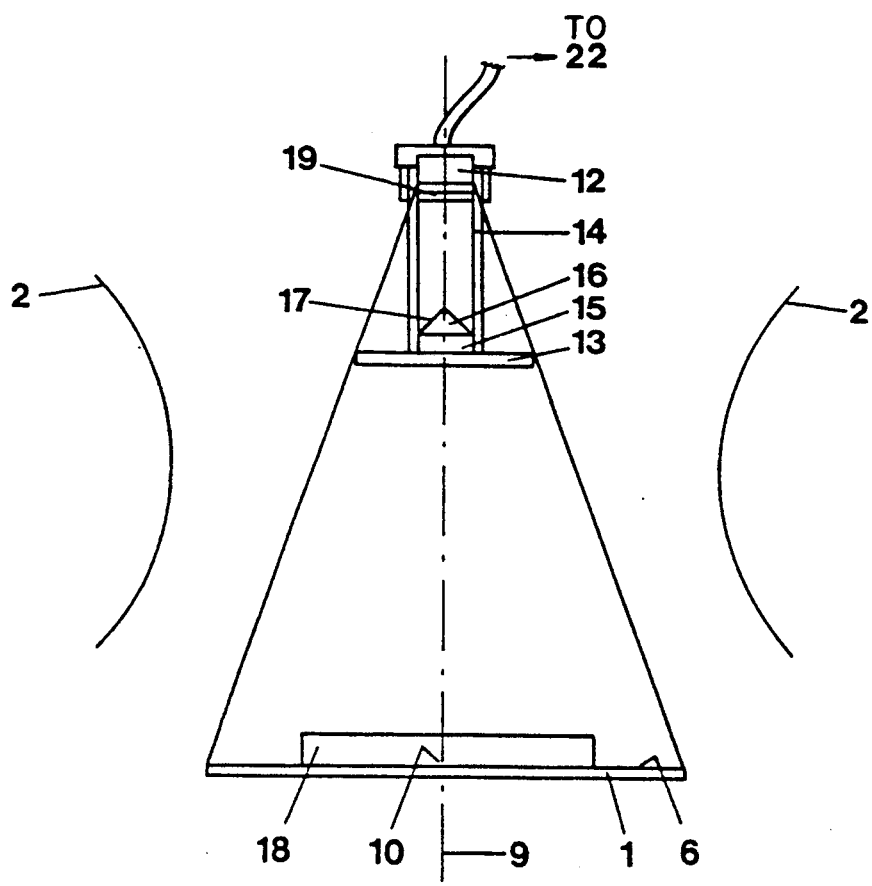
FIG. 3 is a schematic diagram of light quantity measurement in the irradiation device of FIGS. 1 and 2.

Photocell 12 is at a first end of a light conduit. In the embodiment of FIG. 3 this is a hollow cylinder 14 made of quartz glass and screen 13 is fastened to the end of cylinder 14 facing sample holder 1. For this purpose, screen 13 may have a cylindrical portion 15 which slips into the interior of hollow cylinder 14. On the inner surface of screen 13 and on the end of hollow cylinder 14, a reflector 16 is arranged whose reflective surface 17 forms a cone with the point of this cone coinciding with axis 9. By means of this light conduit in the form of hollow cylinder 14, in conjunction with reflector 16 and screen 13, photocell 12 receives only radiation coming directly from lamps 2 and the photocell is protected from radiation which reflect from sample holder 1 or body 18 being irradiated (see FIG. 2) by means of screen 13 which intercepts such reflections.

As FIG. 1 shows, reflector 16 is arranged above sample holder 1 at such a height that it is below the upper ends of irradiation lamps 2. This assures that reflector 16 receives radiation from each irradiation lamp 2 and reflects this radiation on to photocell 12. In order to restrict the radiation reaching photocell 12 to the wavelength range which is effective for polymerization of the bodies to be hardened, one or more filters 19 are provided directly in front of photocell 12. In the embodiment of the light conduit according to FIG. 3, the filters are in hollow cylinder 14 within which photocell 12 is located.

Figure 4:
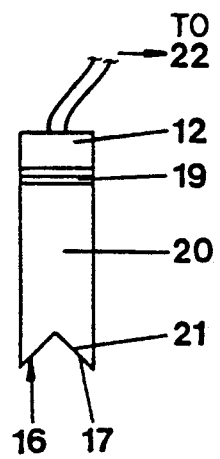
FIGS. 4 and 5 illustrate two different embodiments of the photocell shown in the irradiation device of FIGS. 1 and 2.

FIG. 4 illustrates a section through a light conduit modified from the FIG. 3 embodiment. In this embodiment, a lengthened solid cylinder 20 is provided on whose first end filter 19 and photocell 12 are arranged, while the opposite end has a conical tapped surface 21 coated with reflective material 17 to form reflector 16.

Figure 5:
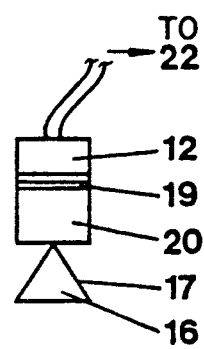

FIG. 5 illustrates another embodiment having a solid cylinder 20 of quartz glass which is somewhat shorter than solid cylinder 20 of FIG. 4; in this embodiment, reflector 16 is a separate component on the end of solid cylinder 20. For simplicity of illustration, screen 13, as shown in FIG. 3, is not illustrated in FIGS. 4 and 5.

Figure 6:
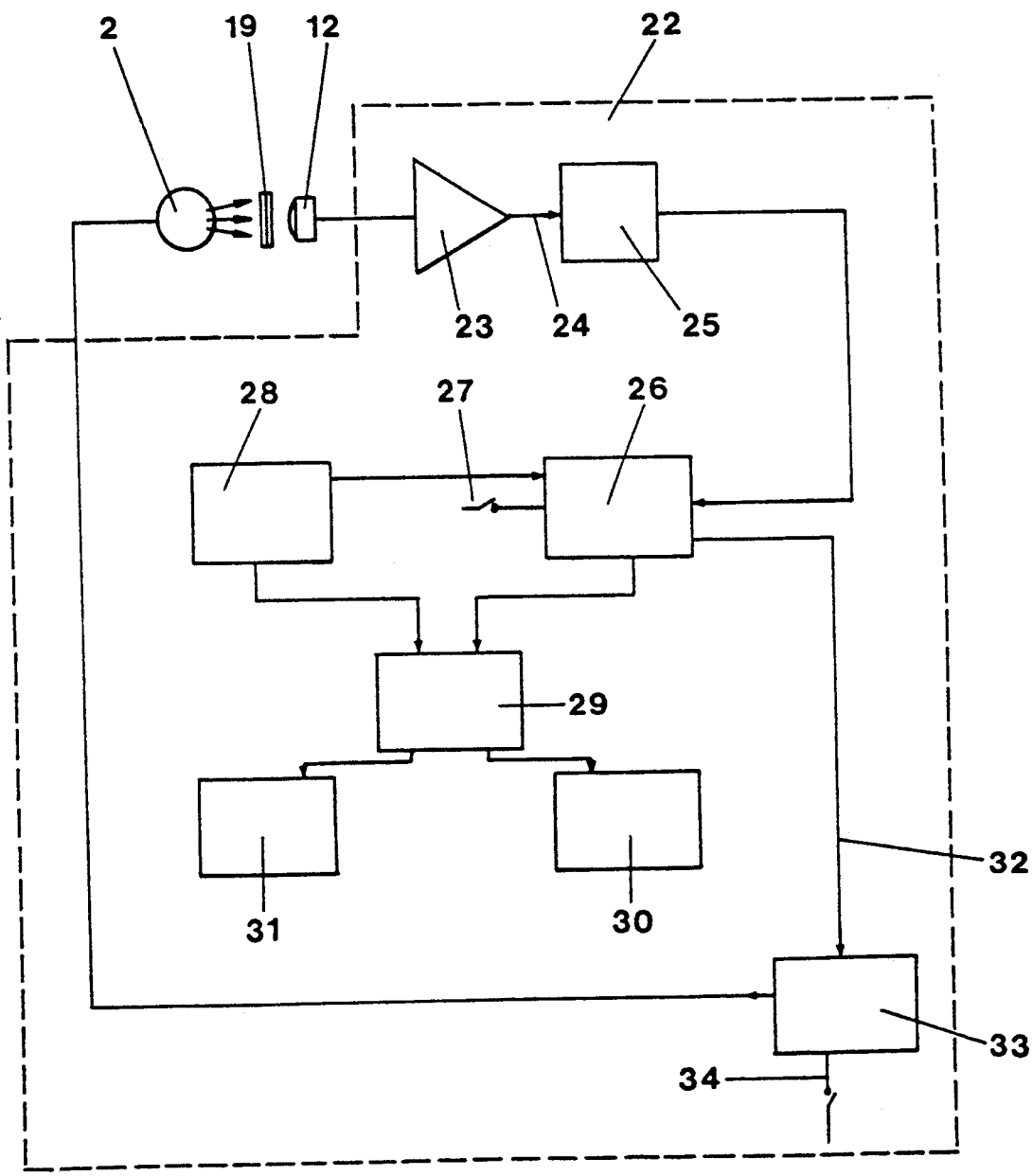
FIG. 6 is a schematic block diagram of the control circuit for carrying out the method of the invention.

As shown in FIG. 6, downstream of photocell 12, a control unit 22 is provided. Control unit 22 features an amplifier 23 whose output 24 is connected to a voltage to frequency converter 25. In amplifier 23, the voltage signal of photocell 12 is amplified and in the downstream voltage to frequency converter 25, transformed into an intensity-dependent frequency. This frequency can, if desired, be divided by frequency dividers which are well known in the art and need not be illustrated here. For example, a frequency divided to achieve a pulse length of about one pulse per second can be fed to a digital actual value counter 26. Before beginning of the radiation, counter 26 can be reset to 0 by pressing a reset button 27. Counter 26 counts the incident pulses and compares the resulting value with a predetermined preset or desired value stored in preset value memory 28. A preset value and actual value are continuously fed through a display decoder 29 to respective actual value display 30 and command value display 31. Once the predetermined radiation amount stored in preset value memory 28 is reached, counter 26 and memory 28 send out a control pulse over a control line 32 to a stop/start unit 33. Unit 33 interrupts the power supply to irradiation lamps 2, for example using relays (not shown).

The irradiation process can be started by pressing a start button 34 associated with start/stop unit 33. If the irradiation intensity of irradiation lamps 2, and thus the radiation passing through filters 19, diminishes, the frequency of the pulses from voltage-to-frequency converter 25 will also diminish, resulting in an increase in the total irradiation or polymerization time required to reach the command value. From irradiation process to radiation process, the irradiation time is corrected in dependence upon the irradiation intensity, so that reproducible irradiation processes are obtained. The result of the irradiation, and thus the result of the hardening, is independent of fluctuations in supply voltage, alterations in irradiation lamps 2, shifting of spectral output, burn out or aging of lamps, soiling of irradiation lamps 2 or their associated reflector surfaces. A complete polymerization of the bodies to be polymerized is assured.

We claim:

1. Apparatus for obtaining optimum photopolymerization of a body from dental plastic, comprising
a generally planar sample holder (1);
at least one radiation source (2) arranged at a predetermined distance from the plane of said sample holder to irradiate a body (18) placed on said sample holder;
a photocell (12) detecting intensity of radiation from said at least one radiation source;
a screen (13) disposed between said photocell (12) and said body (18), thereby shielding said photocell against radiation reflected from said body (18);
a control unit (22) connected to an output of said photocell and controlling cumulative radiation exposure;
said photocell (12) being so arranged in relation to said body (18) and to said screen (13) that said photocell receives radiation directly from said at least one source (2) and substantially no radiation reflected from said body (18); and
means (33) in said control unit (22) for interrupting power supply to said radiation source (2) when a predetermined cumulative radiation exposure is reached.

2. Apparatus according to claim 1, further comprising a reflector (16) arranged adjacent said photocell (12) for reflecting light from said at least one radiation source (2) into said photocell.

3. Apparatus according to claim 1, further comprising
at least one selected-wavelength-range-transmissive filter (19) arranged in front of said photocell.

4. Apparatus according to claim 2, further comprising
a light conduit (14, 20) located with said photocell at one end thereof and said reflector (16) at its other end.

5. Apparatus according to claim 4, wherein said light conduit is a solid cylinder (20) of glassy material.

6. Apparatus according to claim 4, wherein said light conduit is a hollow cylinder (14).

7. Apparatus according to claim 4, wherein said light conduit comprises quartz glass.

8. Apparatus according to claim 1, wherein said photocell is located centrally above said sample holder (1).

9. Apparatus according to claim 1, wherein more than one radiation source is provided, arranged symmetrically about an axis (9) between said sample holder (1) and said photocell (12).

10. Apparatus according to claim 2, wherein said reflector (16) has a reflective surface (17) which is conical.

11. Apparatus according to claim 5, wherein said solid cylinder (20) has a conical recess (21) whose inner surface (17) is coated with reflective material.

12. Apparatus according to claim 6, wherein
a conical reflector (17) is located in one end of said hollow cylinder (14).

13. Apparatus according to claim 1, wherein said control unit (22) includes an amplifier (23) connected to the photocell output, a voltage-to-frequency converter (25) connected to an output of said amplifier, a counter (26) connected to an output of said converter, a command value memory (28) connected to the counter, and means (33) connected to an output of said counter (26) for interrupting power supply to said at least one radiation source.

14. Apparatus according to claim 13, wherein said means for interrupting is a start or stop unit (33).